US007002114B2

(12) United States Patent
He et al.

(10) Patent No.: US 7,002,114 B2
(45) Date of Patent: Feb. 21, 2006

(54) METHODS AND APPARATUS FOR A VARIABLE RESISTOR CONFIGURED TO COMPENSATE FOR NON-LINEARITIES IN A HEATING ELEMENT CIRCUIT

(75) Inventors: Mengtao Pete He, Scottsdale, AZ (US); Carl Triplett, Scottsdale, AZ (US); Mary J. Conway, Phoenix, AZ (US); David Rinaldis, Longmont, CO (US); Michael Strasser, Layette, CA (US)

(73) Assignee: The Dial Corporation, Scottsdale, AZ (US)

( * ) Notice: Subject to any disclaimer, the term of this patent is extended or adjusted under 35 U.S.C. 154(b) by 2 days.

(21) Appl. No.: 10/648,571

(22) Filed: Aug. 26, 2003

(65) Prior Publication Data

US 2004/0129695 A1 Jul. 8, 2004

Related U.S. Application Data

(60) Provisional application No. 60/407,392, filed on Aug. 30, 2002.

(51) Int. Cl.
 *H05B 1/02* (2006.01)
 *H01C 10/44* (2006.01)
(52) U.S. Cl. .................. 219/504; 338/89; 338/139; 338/24; 219/482; 219/488
(58) Field of Classification Search .................. 338/89, 338/138, 139, 24; 219/504, 482, 428; 392/392, 392/393, 403
 See application file for complete search history.

(56) References Cited

U.S. PATENT DOCUMENTS 1,836,600 A 12/1931 Jones
3,262,290 A 7/1966 Huber
3,284,697 A * 11/1966 May ............................ 338/89
3,336,558 A * 8/1967 Wright ....................... 338/138

(Continued)

FOREIGN PATENT DOCUMENTS

DE 35 35 564 5/1986

(Continued)

OTHER PUBLICATIONS

PCT International Search Report issued Dec. 17, 2003 for International Application No. PCT/US03/26511, International Filing Date Aug. 26, 2003, 4 pages.

(Continued)

*Primary Examiner*—Teresa J. Walberg
(74) *Attorney, Agent, or Firm*—Snell & Wilmer LLP (57) ABSTRACT

An improved variable resistor at least partially compensates for non-linearities in an electrical circuit containing a heating element, for example, a thin-film heating element. A controllable heater includes a heating element, a voltage source (for example, a standard AC electrical outlet) coupled to the heating element, and a variable resistor coupled to the heating element and voltage source. The variable resistor includes a fixed resistive element (for example, one or more thin-film resistors) and a moveable element such as a slider control. The moveable element adjustably contacts the fixed resistive element at a contact point associated with the position such that the variable resistor has a resistance that is at least partially non-linearly related to the position, but wherein the heating element has a dissipated power that is at least partially linearly related to the position of the variable resistor. Such a system may be used in conjunction with a vapor-delivery device to provide more linear control over the intensity of fragrance provided within an environment.

16 Claims, 8 Drawing Sheets

U.S. PATENT DOCUMENTS

| | | | |
|---|---|---|---|
| 3,564,475 A * | 2/1971 | Fujii et al. ............... 338/89 |
| 3,723,938 A * | 3/1973 | Gramm ................ 338/92 |
| 3,748,438 A | 7/1973 | Costello |
| 3,780,260 A | 12/1973 | Eisner |
| 3,895,928 A | 7/1975 | Moran |
| 3,908,905 A | 9/1975 | Von Philipp et al. |
| 3,923,458 A | 12/1975 | Moran |
| 3,948,445 A | 4/1976 | Andweg |
| 4,017,030 A | 4/1977 | Coplan et al. |
| 4,035,787 A * | 7/1977 | Hornung ............... 432/36 |
| 4,037,353 A | 7/1977 | Hennart et al. |
| 4,084,079 A | 4/1978 | Costello |
| 4,111,655 A | 9/1978 | Quincey |
| 4,123,741 A * | 10/1978 | Kiyono et al. ........... 338/138 |
| 4,165,835 A | 8/1979 | Dearling |
| 4,171,340 A | 10/1979 | Nishimura et al. |
| 4,208,012 A | 6/1980 | Dutcher |
| 4,214,146 A | 7/1980 | Schimanski |
| 4,220,281 A | 9/1980 | Martens, III et al. |
| 4,228,124 A | 10/1980 | Kashihara et al. |
| 4,237,442 A * | 12/1980 | Carter ................ 338/138 |
| 4,242,969 A | 1/1981 | Steigerwald et al. |
| 4,283,704 A * | 8/1981 | Ohtani et al. ........... 338/138 |
| 4,293,173 A | 10/1981 | Tricca |
| 4,294,778 A | 10/1981 | DeLuca |
| 4,346,059 A | 8/1982 | Spector |
| 4,391,781 A | 7/1983 | Van Lit |
| 4,408,813 A | 10/1983 | Koehler |
| 4,413,779 A | 11/1983 | Santini |
| 4,415,797 A | 11/1983 | Choustoulakis |
| 4,425,302 A | 1/1984 | Pons Pons |
| 4,435,691 A * | 3/1984 | Ginn ................ 338/125 |
| 4,467,117 A | 8/1984 | Zobele |
| 4,518,212 A | 5/1985 | Rumble |
| 4,530,556 A | 7/1985 | Bonus |
| 4,537,351 A | 8/1985 | Wilson |
| 4,544,592 A | 10/1985 | Spector |
| 4,549,250 A | 10/1985 | Spector |
| 4,556,539 A | 12/1985 | Spector |
| 4,571,485 A | 2/1986 | Spector |
| 4,574,181 A | 3/1986 | Spector |
| 4,595,564 A | 6/1986 | Spector et al. |
| 4,631,387 A | 12/1986 | Glucksman |
| 4,658,985 A | 4/1987 | Madsen et al. |
| 4,660,764 A | 4/1987 | Joyaux et al. |
| 4,662,679 A | 5/1987 | Franck |
| 4,675,504 A | 6/1987 | Suhajda |
| 4,686,353 A | 8/1987 | Spector |
| 4,694,272 A * | 9/1987 | Maisch ................ 338/138 |
| 4,695,434 A | 9/1987 | Spector |
| 4,703,155 A | 10/1987 | Suhajda |
| 4,707,336 A | 11/1987 | Jones |
| 4,714,984 A | 12/1987 | Spector |
| 4,718,856 A | 1/1988 | Pinkerton et al. |
| 4,725,712 A | 2/1988 | Schroeder |
| 4,731,520 A | 3/1988 | Glucksman |
| 4,731,522 A | 3/1988 | Manchester |
| 4,732,321 A | 3/1988 | Dolan |
| 4,734,560 A | 3/1988 | Bowen |
| 4,739,928 A | 4/1988 | O'Neil |
| 4,743,406 A | 5/1988 | Steiner et al. |
| 4,753,389 A | 6/1988 | Davis |
| 4,777,345 A | 10/1988 | Manchester |
| 4,780,286 A | 10/1988 | Parent et al. |
| 4,795,883 A | 1/1989 | Glucksman et al. |
| 4,798,935 A | 1/1989 | Pezaris |
| 4,800,239 A | 1/1989 | Hill |
| 4,801,271 A | 1/1989 | Piper |
| 4,804,821 A | 2/1989 | Glucksman |
| 4,808,347 A | 2/1989 | Dawn |
| 4,816,973 A | 3/1989 | Atalla et al. |
| 4,830,791 A | 5/1989 | Muderlak et al. |
| 4,837,421 A | 6/1989 | Luthy |
| 4,849,606 A | 7/1989 | Martens, III et al. |
| 4,853,517 A | 8/1989 | Bowen et al. |
| 4,878,615 A | 11/1989 | Losi |
| 4,886,469 A | 12/1989 | Jseng |
| 4,915,301 A | 4/1990 | Munteanu |
| 4,919,981 A | 4/1990 | Levey et al. |
| 4,931,224 A | 6/1990 | Holzner, Sr. |
| 4,931,258 A | 6/1990 | Zlotnik et al. |
| 4,968,456 A | 11/1990 | Muderlak et al. |
| D315,789 S | 3/1991 | Muderlak |
| 4,998,671 A | 3/1991 | Leifheit |
| 5,004,435 A | 4/1991 | Jammet |
| 5,014,913 A | 5/1991 | Hoyt et al. |
| 5,015,442 A | 5/1991 | Hirai |
| 5,029,729 A | 7/1991 | Madsen et al. |
| 5,038,394 A | 8/1991 | Hasegawa et al. |
| 5,050,798 A | 9/1991 | Sullivan |
| 5,106,317 A | 4/1992 | Taylor |
| 5,111,477 A | 5/1992 | Muderlak |
| 5,115,975 A | 5/1992 | Shilling |
| 5,121,881 A | 6/1992 | Lembeck |
| 5,126,078 A | 6/1992 | Steiner et al. |
| 5,136,684 A | 8/1992 | Lonker et al. |
| 5,147,582 A | 9/1992 | Holzner, Sr. et al. |
| 5,148,984 A | 9/1992 | Bryson, Jr. et al. |
| 5,175,791 A | 12/1992 | Muderlak et al. |
| 5,196,171 A | 3/1993 | Peltier |
| 5,201,025 A | 4/1993 | Landesberg |
| 5,217,696 A | 6/1993 | Wolverton et al. |
| 5,220,636 A | 6/1993 | Chang |
| 5,222,186 A | 6/1993 | Schimanski et al. |
| 5,223,182 A | 6/1993 | Steiner et al. |
| 5,233,680 A | 8/1993 | Fussell |
| 5,239,610 A | 8/1993 | Shao |
| 5,240,426 A | 8/1993 | Barla |
| 5,285,014 A | 2/1994 | Gilchrist |
| 5,290,546 A | 3/1994 | Hasegawa et al. |
| 5,295,845 A | 3/1994 | Changxing |
| 5,314,669 A | 5/1994 | Hamilton |
| 5,320,542 A | 6/1994 | Cheng |
| 5,339,065 A * | 8/1994 | Slenker ................ 338/133 |
| 5,342,584 A | 8/1994 | Fritz et al. |
| 5,373,581 A | 12/1994 | Smith ................ 392/390 |
| 5,375,728 A | 12/1994 | West |
| 5,376,338 A | 12/1994 | Zlotnik |
| 5,382,410 A | 1/1995 | Peltier |
| D355,251 S | 2/1995 | Paulovich et al. |
| 5,394,506 A | 2/1995 | Stein et al. |
| 5,402,517 A | 3/1995 | Gillett et al. |
| D357,330 S | 4/1995 | Wong et al. |
| 5,431,859 A | 7/1995 | Tobin |
| 5,431,885 A | 7/1995 | Zlotnik et al. |
| 5,445,802 A | 8/1995 | Wendelken |
| 5,465,198 A | 11/1995 | Kellogg |
| 5,480,591 A | 1/1996 | Lagneaux et al. |
| 5,481,442 A | 1/1996 | Dickie et al. |
| 5,484,086 A | 1/1996 | Pu |
| 5,498,397 A | 3/1996 | Horng |
| 5,521,357 A | 5/1996 | Lock et al. |
| 5,522,008 A | 5/1996 | Bernard |
| 5,547,616 A | 8/1996 | Dancs et al. |
| 5,556,192 A | 9/1996 | Wang |
| 5,567,361 A | 10/1996 | Harper |
| 5,574,821 A | 11/1996 | Babasade |
| 5,575,992 A | 11/1996 | Kunze |
| 5,577,156 A | 11/1996 | Costello ................ 392/390 |
| 5,591,395 A | 1/1997 | Schroeder et al. |
| 5,624,230 A | 4/1997 | Taylor et al. |
| 5,634,806 A | 6/1997 | Hahn |
| 5,647,052 A | 7/1997 | Patel et al. ............... 392/390 |
| 5,647,053 A | 7/1997 | Schroeder et al. |

| Patent No. | Date | Inventor(s) | Class |
|---|---|---|---|
| 5,651,942 A | 7/1997 | Christinsen | |
| 5,662,835 A | 9/1997 | Collingwood | |
| 5,664,958 A | 9/1997 | Chadwick et al. | |
| 5,700,430 A | 12/1997 | Bonnema et al. | |
| 5,735,460 A | 4/1998 | Eisenbraun | |
| 5,749,520 A | 5/1998 | Martin et al. | |
| 5,750,498 A | 5/1998 | Soeda et al. | |
| 5,765,751 A | 6/1998 | Joshi | |
| 5,788,155 A | 8/1998 | Martin et al. | |
| 5,788,931 A | 8/1998 | Munoz Quintana | |
| 5,796,914 A | 8/1998 | Gatzemeyer et al. | 392/390 |
| 5,805,768 A | 9/1998 | Schwartz et al. | |
| 5,810,265 A | 9/1998 | Cornelius et al. | |
| 5,813,873 A | 9/1998 | McBain et al. | |
| 5,832,648 A | 11/1998 | Malone | |
| 5,873,529 A | 2/1999 | Johnson | |
| 5,875,968 A | 3/1999 | Miller et al. | |
| 5,884,808 A | 3/1999 | Muderlak et al. | |
| 5,899,381 A | 5/1999 | Gordon et al. | |
| 5,903,710 A | 5/1999 | Wefler et al. | 392/392 |
| 5,926,614 A | 7/1999 | Steinel | |
| 5,928,605 A | 7/1999 | Bonnema et al. | |
| 5,932,204 A | 8/1999 | Joshi | |
| 5,937,140 A | 8/1999 | Leonard et al. | |
| 5,940,577 A | 8/1999 | Steinel | |
| 5,944,223 A | 8/1999 | Klima et al. | |
| 5,945,094 A | 8/1999 | Martin et al. | |
| 5,955,701 A | 9/1999 | Schockner et al. | |
| 5,957,701 A | 9/1999 | McMillin | |
| 5,970,643 A | 10/1999 | Gawel, Jr. | |
| 5,976,503 A | 11/1999 | Martin et al. | |
| 5,998,735 A | 12/1999 | Patterson, Jr. | |
| 6,021,254 A | 2/2000 | Hunter | 392/390 |
| 6,031,967 A | 2/2000 | Flashinski et al. | 392/390 |
| 6,032,930 A | 3/2000 | Calino | |
| 6,036,536 A | 3/2000 | Chiu | |
| 6,044,202 A | 3/2000 | Junkel | 392/390 |
| 6,045,374 A | 4/2000 | Candeloro | |
| 6,050,551 A | 4/2000 | Anderson | |
| 6,051,788 A | 4/2000 | Nichols | |
| 6,078,728 A | 6/2000 | O'Rourke et al. | 392/390 |
| 6,085,026 A | 7/2000 | Hammons et al. | 392/390 |
| 6,097,881 A | 8/2000 | DeWitt et al. | 392/392 |
| 6,099,137 A | 8/2000 | McCormick et al. | |
| 6,101,315 A | 8/2000 | Steinel, Jr. | 392/386 |
| 6,104,866 A | 8/2000 | DeWitt et al. | 392/390 |
| 6,104,867 A | 8/2000 | Stathakis et al. | |
| D430,659 S | 9/2000 | Zaraboza et al. | |
| 6,123,935 A | 9/2000 | Wefler et al. | |
| 6,141,496 A * | 10/2000 | Sundberg et al. | 392/392 |
| 6,148,143 A | 11/2000 | Steinel, Jr. | 392/390 |
| 6,156,088 A | 12/2000 | Cardarelli | |
| 6,197,262 B1 | 3/2001 | Del Ben | |
| 6,197,263 B1 | 3/2001 | Blount | |
| 6,227,118 B1 | 5/2001 | Nance | |
| 6,236,807 B1 | 5/2001 | Ruffolo et al. | 392/390 |
| 6,249,645 B1 | 6/2001 | Smith | 392/403 |
| 6,254,011 B1 * | 7/2001 | Kelly et al. | 237/12.3 R |
| 6,254,065 B1 | 7/2001 | Ehrensperger et al. | |
| 6,264,548 B1 | 7/2001 | Payne, Jr. et al. | |
| 6,269,979 B1 | 8/2001 | Dumont | |
| 6,270,720 B1 | 8/2001 | Mandish | |
| 6,275,651 B1 | 8/2001 | Voit | 392/403 |
| 6,278,840 B1 | 8/2001 | Basaganas Millan | 392/390 |
| 6,285,830 B1 | 9/2001 | Basaganas Millan | 392/395 |
| 6,289,176 B1 | 9/2001 | Martter et al. | 392/392 |
| 6,302,559 B1 | 10/2001 | Warren | |
| 6,315,959 B1 | 11/2001 | Mandish | |
| 6,328,791 B1 | 12/2001 | Pillion et al. | |
| 6,342,676 B1 | 1/2002 | Ha | |
| 6,349,168 B1 | 2/2002 | Jaworski | 392/392 |
| 6,352,210 B1 | 3/2002 | Requejo | |
| 6,354,513 B1 | 3/2002 | Basaganas Millan | |
| 6,361,752 B1 | 3/2002 | Demarest et al. | |
| 6,364,673 B1 | 4/2002 | Lee | |
| 6,368,564 B1 | 4/2002 | Smith | |
| 6,371,815 B1 | 4/2002 | Wetzel et al. | |
| 6,374,044 B1 | 4/2002 | Freidel | 392/390 |
| 6,374,045 B1 | 4/2002 | Basaganas Millan | 392/395 |
| 6,381,408 B1 | 4/2002 | Jaworski et al. | 392/392 |
| 6,603,924 B1 | 8/2003 | Brown et al. | 392/390 |
| 6,714,725 B1 | 3/2004 | Grone et al. | 392/392 |
| 2001/0031225 A1 | 10/2001 | Mandish | |
| 2001/0053283 A1 | 12/2001 | Levine et al. | |
| 2002/0144992 A1 | 10/2002 | Vieira | |
| 2003/0138241 A1 | 7/2003 | Ambrosi et al. | |

FOREIGN PATENT DOCUMENTS

| | | |
|---|---|---|
| DE | 41 31 613 | 3/1993 |
| EP | 0 296 807 | 12/1988 |
| EP | 0 669 137 | 8/1995 |
| EP | 0 911 041 | 4/1999 |
| GB | 402507 | 12/1933 |
| GB | 2 356 815 | 6/2001 |
| WO | WO 00 76292 | 12/2000 |
| WO | WO 01 10739 | 2/2001 |
| WO | WO 01/68154 | 9/2001 |
| WO | WO 01/93919 | 12/2001 |

OTHER PUBLICATIONS

PCT International Search Report issued Apr. 21, 2004 for International Application No. PCT/US03/26754, International Filing Date Aug. 28, 2003, 4 pages.

PCT International Search Report issued Nov. 12, 2003 for International Application No. PCT/US03/25245, International Filing Date Aug. 13, 2003, 4 pages.

PCT International Search Report issued Oct. 7, 2003 for International Application No. PCT/US03/04082, International Filing Date Feb. 12, 2003, 8 pages.

PCT International Search Report issued Dec. 16, 2003 for International Application No. PCT/US03/25244, International Filing Date Aug. 13, 2003, 3 pages.

PCT International Search Report issued Dec. 16, 2003 for International Application No. PCT/US03/25246, International Filing Date Aug. 13, 2003, 3 pages.

PCT International Search Report issued Dec. 19, 2003 for International Application No. PCT/US03/25243, International Filing Date Aug. 13, 2003, 4 pages.

Brochure-"Decora Devices," by Leviton, date unknown, Section A, pps. A1-A36.

PCT Written Opinion issued Nov. 22, 2004 for International Application No. PCT/US03/26511, International Filing Date Aug. 26, 2003, 4 pages.

PCT International Preliminary Examination Report issued Apr. 6, 2005 for International Application No. PCT/US03/26511, International Filing Date Aug. 26, 2003, 7 pages.

* cited by examiner

METHODS AND APPARATUS FOR A VARIABLE RESISTOR CONFIGURED TO COMPENSATE FOR NON-LINEARITIES IN A HEATING ELEMENT CIRCUIT

CROSS-REFERENCE TO RELATED APPLICATIONS

This application claims priority to U.S. Provisional Patent Application Ser. No. 60/407,392 filed Aug. 30, 2002 and entitled "Method and Apparatus for a Variable Resistor Configured to Compensate for Non-Linearities in a Heating Element Circuit," and is incorporated herein by reference.

FIELD OF INVENTION

The present invention generally relates to the control of heating elements and, more particularly, to an improved variable resistor configured to at least partially compensate for non-linearities in an electrical circuit containing a heating element.

BACKGROUND OF THE INVENTION

It is desirable to employ relatively compact and simple passive components to provide control of resistive loads. For example, variable resistors are often employed to provide some measure of control over heating elements and the like which are typically configured in series with an appropriate voltage source. In this way, the variable resistor effectively functions as a controllable voltage divider.

Certain advantages would be provided by a variable resistor that could compensate for non-linearities inherent in even simple heating element circuits. That is, as both the total current through the resistive heating element as well as the voltage across the heating element are a function of the variable resistance, the relationship between dissipated power in the heating element is related to the position of the variable resistor in a non-trivial manner. This can be unsatisfactory in many applications where the consumer or user has an expectation that the application in which the variable resistor is deployed should have a linear response with respect to the position of the variable resistor (e.g., a slider, dial, knob, or other such user interface mechanically coupled to the variable resistor).

One such application where an improved variable resistor would be advantageous is in the field of vapor-dispensing devices. In general, vapor-dispensing products typically include a volatizable material and a transport system configured to facilitate evaporation of the volatizable material into the surrounding air. For example, in some systems, a liquid is contained in a reservoir bottle; in others, a wax material is used. The housing, which may protrude from a wall outlet (and may thereby supply the voltage source), facilitates the evaporation of the volatizable material into the environment. In such devices, the heating element is thermally coupled to the volatizable material and/or any wicks or other material delivery components. In such a case, it would be desirable for the evaporation rate to be at least partially linear with respect to the position of the variable resistor.

SUMMARY OF THE INVENTION

While the way that the present invention addresses the disadvantages of the prior art will be discussed in greater detail below, in general, the present invention provides an improved variable resistor configured to at least partially compensate for non-linearities in an electrical circuit containing a heating element, for example, a thin-film heating element.

In accordance with one embodiment of the present invention, a controllable heater includes a heating element, a voltage source (for example, a standard AC electrical outlet) coupled to the heating element, and a variable resistor coupled to the heating element and voltage source. The variable resistor includes a fixed resistive element (for example, one or more thin-film resistors) and a moveable element such as a slider control. The moveable element adjustably contacts the fixed resistive element at a contact point associated with the position such that the variable resistor has a resistance that is at least partially non-linearly related to the position, but wherein the heating element has a dissipated power that is at least partially linearly related to the position of the variable resistor.

In accordance with one embodiment of the present invention, the fixed element may include one or more thin-film resistors having a width that varies continuously or discontinuously over its length. Such a heater may be used, for example, in conjunction with a vapor-dispensing device that is thermally coupled to the heater, and which may contain various volatizable materials such as oils, waxes, or the like.

BRIEF DESCRIPTION OF THE DRAWING FIGURES

A more complete understanding of the present invention may be derived by referring to the detailed description when considered in connection with the Figures, where like reference numbers refer to similar elements throughout the Figures, and.

DETAILED DESCRIPTION OF EXEMPLARY EMBODIMENTS OF THE INVENTION

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in the function and arrangement of the elements described in these embodiments without departing from the scope of the invention as set forth herein. For example, in the context of the present invention, the method and apparatus described herein may find particular use in connection with vapor-delivery systems such as air-fresheners and the like. Generally speaking, however, the present invention may be used in conjunction with any application requiring a controllable heat source such as a thin film resistor heat source.

Figure 1:
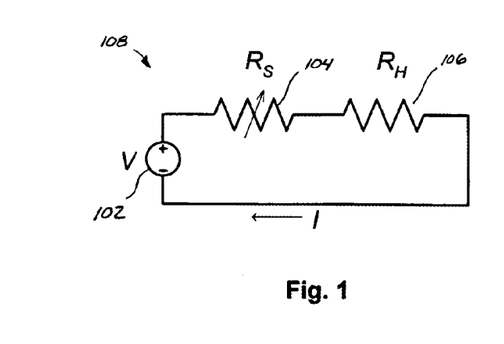
FIG. 1 illustrates a heating circuit in which the present invention may be deployed.

FIG. 1 depicts an exemplary circuit 108 in accordance with the present invention. In general, a voltage source 102 having a voltage V (e.g., an AC or DC source) is connected in series with a resistive heating element 106 (having an associated voltage $V_H$ and resistance $R_H$) and a variable resistor 104 (having an associated voltage $V_S$ and resistance $R_S$). A current I is responsive to the total circuit resistance, e.g., $R_S + R_H$.

The nature of this circuit is such that the power dissipated by heater 106 is non-linearly related to the resistance of variable resistor 104. This is due to the fact that the dissipated power of heater 106 is a function of the total current in the circuit as well as the voltage across heater 106, and both of these values are a function of the resistance of variable resistor 104. More particularly, the dissipated power $P_H$ of heater 106 is given by:

$$P_H = IV_H = I(V - V_S) \tag{1}$$

while the total circuit current is given by:

$$I = \frac{V}{R_S + R_H} \tag{2}$$

Substituting equation (2) into equation (1) and simplifying, the power generated and dissipated by the heater can be expressed as an inverse polynomial given by:

$$P_H = C_1 \left( \frac{1}{R_S^2 + C_2 R_S + C_3} \right) \tag{3}$$

where:

$$C_1 = V^2 R_H, \; C_2 = 2R_H, \; C_3 = R_H^2$$

In view of the relative complexity of equation (3), it is difficult to produce a dissipated power $P_H$ which varies linearly with the position of variable resistor 104. More particularly, referring now to the qualitative graph illustrated in FIG. 2, the power dissipated by heater 106 (curve 202) decreases as the variable resistance increases, but the rate (or slope) of the curve also decreases. As such, less control (or coarser control) of dissipated power is provided at low resistance values, and greater control (or finer control) of dissipated power is provided at high resistance values. Similarly, the power dissipated by variable resistor 104 also varies non-linearly with its own resistance value.

Figure 2:
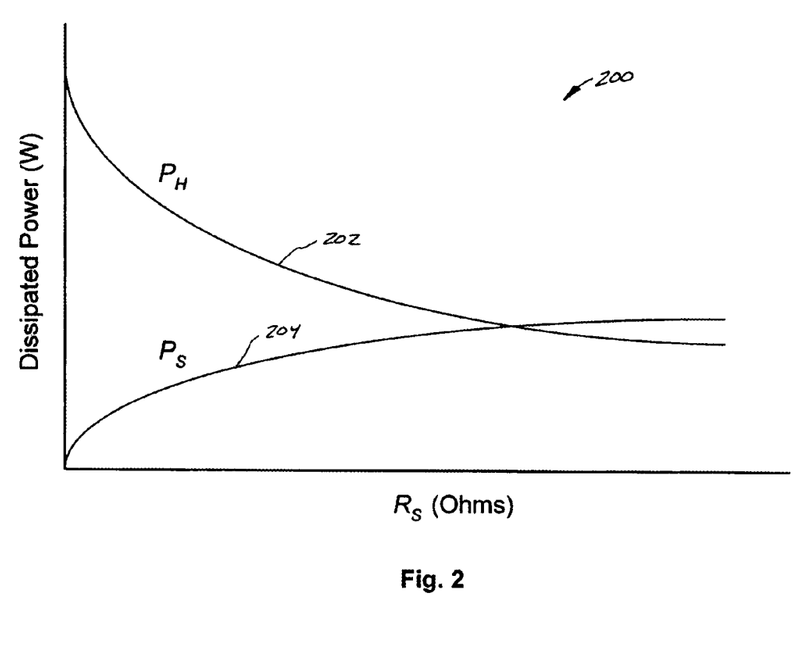
FIG. 2 is a graph depicting the non-linear relationship between variable resistance and dissipated power.

The non-linearities shown in FIG. 2 can lead to unsatisfactory results in a context where a user has an expectation that the controller will behave linearly. That is, a variable resistor 104 might typically include a slider, knob, dial, or other such interface which is manipulated by a user to produce a particular heater setting. These setting may be indicated by words, symbols, tick-marks or any other such indicia. For example, an "H" may be provided at one end of a slider (or one setting of a knob) to indicate a "high" setting (i.e., a low variable resistance value), and an "L" may be provided at the other end of the slider or knob to indicate a "low" setting (i.e., a high variable resistance value). Assuming that the resistance value $R_S$ is a function of a characteristic distance d along a slider such that $R_S = f(d)$, where d is a dimensionless parameter ranging from 0 to 1.0, if the resistance value of the variable resistor varies linearly with position, e.g.:

$$R_S = R_{max} d \tag{4}$$

where $R_{max}$ is the maximum resistance of the device, then the dissipated power of the heater will also vary non-linearly with the slider setting.

Consider, for example, the system of FIG. 1 wherein voltage source 102 is a standard 115 VAC voltage source, the resistance of heater 106 is a relatively constant 4852 Ohms, and the resistance of variable resistor 104 varies linearly from 8232.0 Ohms to 0.0 Ohms as the slider (or other interface) is moved from a "High" setting to a "Low" setting. It can be shown, using equation (3) above, that the dissipated power of heater 106 then varies from 2.73 Watts to 0.37 Watts. However, the mid-point along the heating curve, ((2.73+0.37)/2)=1.55 Watts, occurs at approximately the three-quarter point on the slider, closer to the "High" setting rather than midway between the "High" and "Low" settings.

In accordance with the present invention, however, a variable resistor includes a fixed resistive element and a moveable element configured such that the variable resistor has a resistance that is at least partially non-linearly related to the position of the variable resistor and has a dissipated power that is at least partially linearly related to the position.

Figure 3:
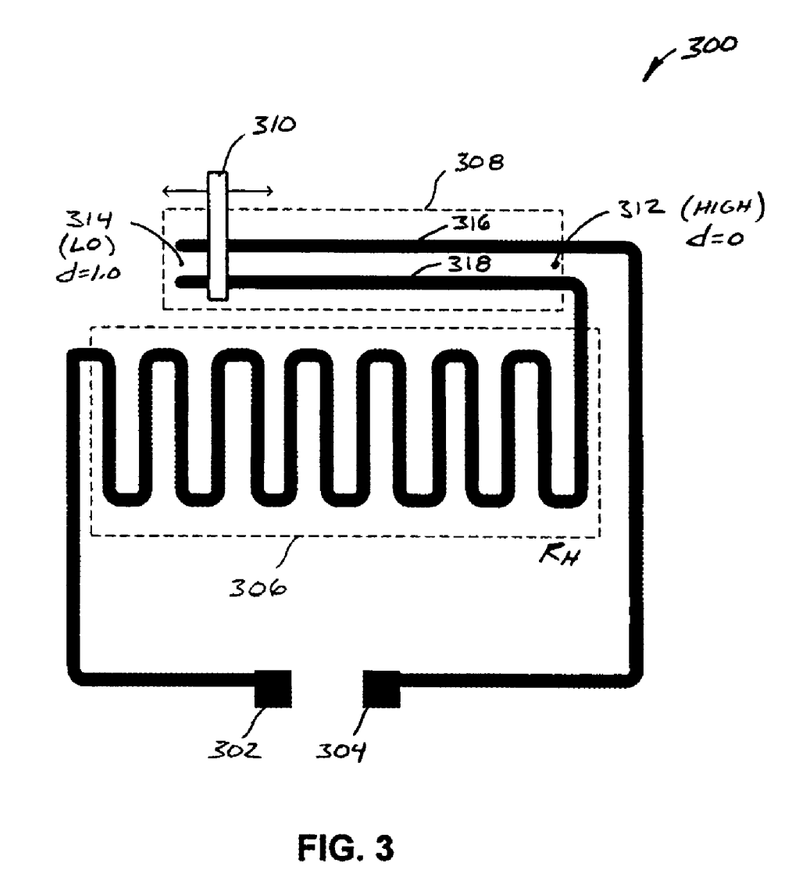
FIG. 3 is a schematic illustration of a heating element and variable resistor in accordance with one embodiment of the present invention.

Referring now to FIG. 3, a controllable heating apparatus 300 suitably includes a heating element 306 operating in series with a variable resistor 308. A pair of terminals 302 and 304 are provided for connecting to an appropriate power source (not shown). Variable resistor 308 includes a moveable element 310 and a fixed resistive element 308. Moveable element 310 (for example, a conductive material such as copper, steel, or the like) is configured to move laterally along fixed resistive element 308 from a low setting 314 to a high setting 312 and makes contact with resistive element 308 at one or more points, depending upon the number of positions that moveable element 310 may occupy. That is, moveable element 310 may move continuously along resistive element 308, or may have a plurality of discrete defined positions along the length of resistive element 308. For example, moveable element 310 may simply have two discrete positions ("High" at position 312, and "Low" at position 314), three discrete positions (the former configuration with an additional "Medium" setting approximately half-way between positions 312 and 314), or any number of discrete positions defined in an arbitrary manner along the length of resistive element 308.

While the moveable element 310 of FIG. 3 is illustrated as a slider, the present invention is not so limited. A variety of devices and interfaces may be used in connection with moveable element 310, including various knobs, dials, screws, thumbwheels, and any other such component currently known or later developed. Furthermore, while the path of moveable element 310 is illustrated as Cartesian (i.e., translation along a line), variable resistor 308 may also be configured in a polar coordinate space, e.g., as a dial having a moveable element 310 of a given radius that rotates around and contacts resistive element 308 at a plurality of characteristic angles. Indeed, any arbitrary path for moveable element 310 may be used.

Heating element 306 suitably includes one or more heating components such as thin-film resistors, coils, and/or the like. In the illustrated embodiment, heating element 306 comprises a serpentine pattern of thin-film resistive material. The resistivity and geometry of heating element 306, as well as the range of currents which are applied to heating element 306 via movement of element 310, may be selected to afford any desired range of temperature values. In an exemplary embodiment, heating element 306 has the following thermal characteristics: a temperature of approximately 140° F. to 160° F. at a "high" setting a temperature of approximately 100° F. to 130° F. at a "medium" setting; and a temperature of approximately 110 to 120° F. at a "low" setting.

Fixed resistive element 308 comprises one or more resistive components such as coil resistors, thin-film resistors, or any other such component now known or later developed. In the illustrated embodiment, resistive element 308 includes two thin-film resistors 316 and 318 configured substantially in parallel from one end (314) to the other end (312) deposited on a suitable substrate 402 (e.g., a plastic or printed-circuit-board (PCB) material). It will be understood, however, that any number and combination of such resistive components may be employed.

Thin-film resistors 316 and 318 suitably comprise any suitable thin-film material, including, for example, TaN, NiCr, or any other such resistive material deposited on substrate 402 in accordance with any conventional or later-developed deposition technique.

The embodiment illustrated in FIG. 3 operates in the following way. As moveable element 310 (or any type of dial, slider, or other component coupled to element 310) is positioned along resistive element 308 (e.g., by a user wishing to change the heater setting), moveable element 310 contacts thin-film resistors 316 and 318 at a corresponding set of points, resulting in a circuit from terminal 302, through heating element 306, through the segment of thin-film resistor 308, through moveable element 310 and the corresponding segment of thin-film resistor 316, and back to terminal 304 which, along with terminal 302, contacts a suitable voltage source (not shown). The resistance of variable resistor 308 is then equal to the sum of the resistances of the two segments of thin-film resistors (316 and 318) extending from the points of contact of moveable element 310 to the "high" setting 312.

As the resistance of variable resistor 308 increases, the total current through the circuit decreases, as does the voltage drop across heating element 306. Consequently, the heat dissipated by heating element 306 decreases. In this way, the dissipated power of heating element 306 may be controlled by the positioning of moveable element 310.

As discussed briefly above, the present invention provides a variable resistor variable resistor exhibiting a resistance that is at least partially non-linearly related to the position of the variable resistor and has a dissipated power that is at least partially linearly related to the position of the variable resistor. In this way, the variable resistor can partially compensate for non-linearities inherent in the circuit. In accordance with one aspect of the present invention, one or more attributes of thin-film resistor 316 and/or 318 may be varied along its length to provided the desired relationship between position and resistance.

Figure 5:
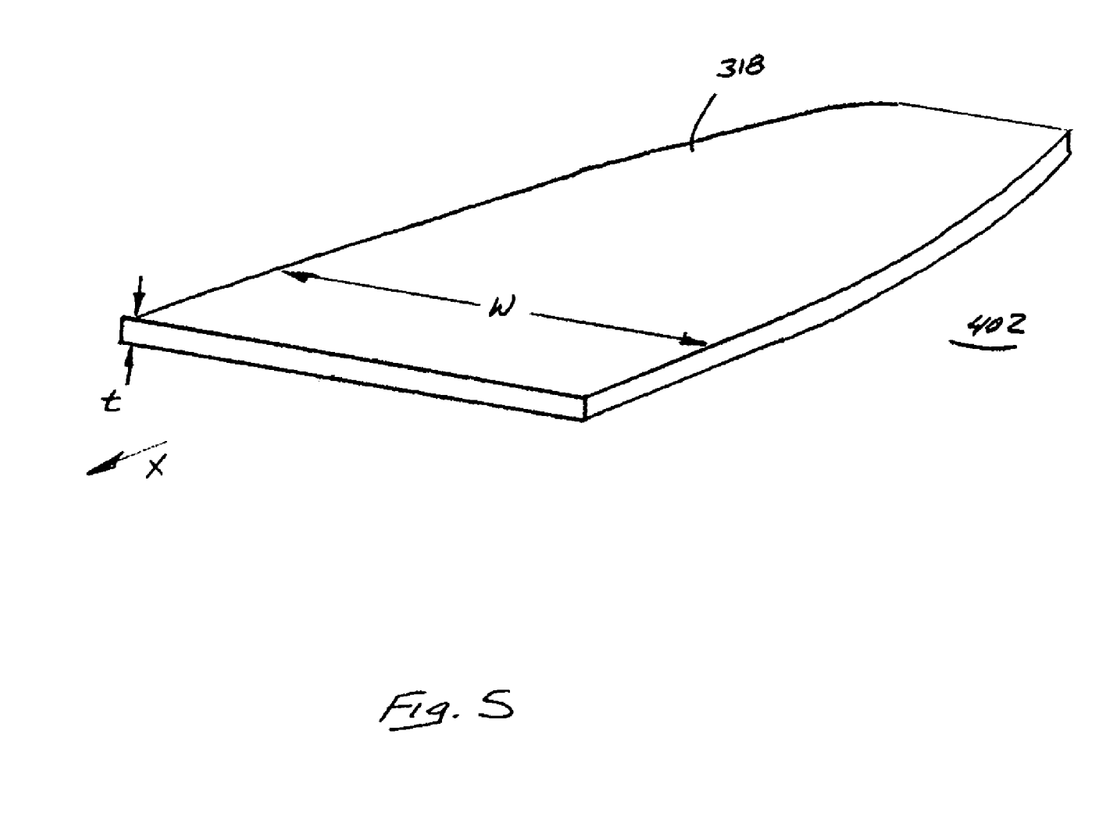
FIG. 5 is an isometric view of an exemplary thin-film resistor.

For example, the resistance of a segment of thin-film material is given by:

$$R_{film} = \frac{\rho d}{wt} \tag{5}$$

where $\rho$ is the film resistivity in ohm·cm, d is the length of the resistor, w is the width of the film, and t is the thickness of the film as shown in FIG. 5. It is then suitable to vary the width, thickness, and/or the resistivity of the thin film resistor over its length.

Figure 4:
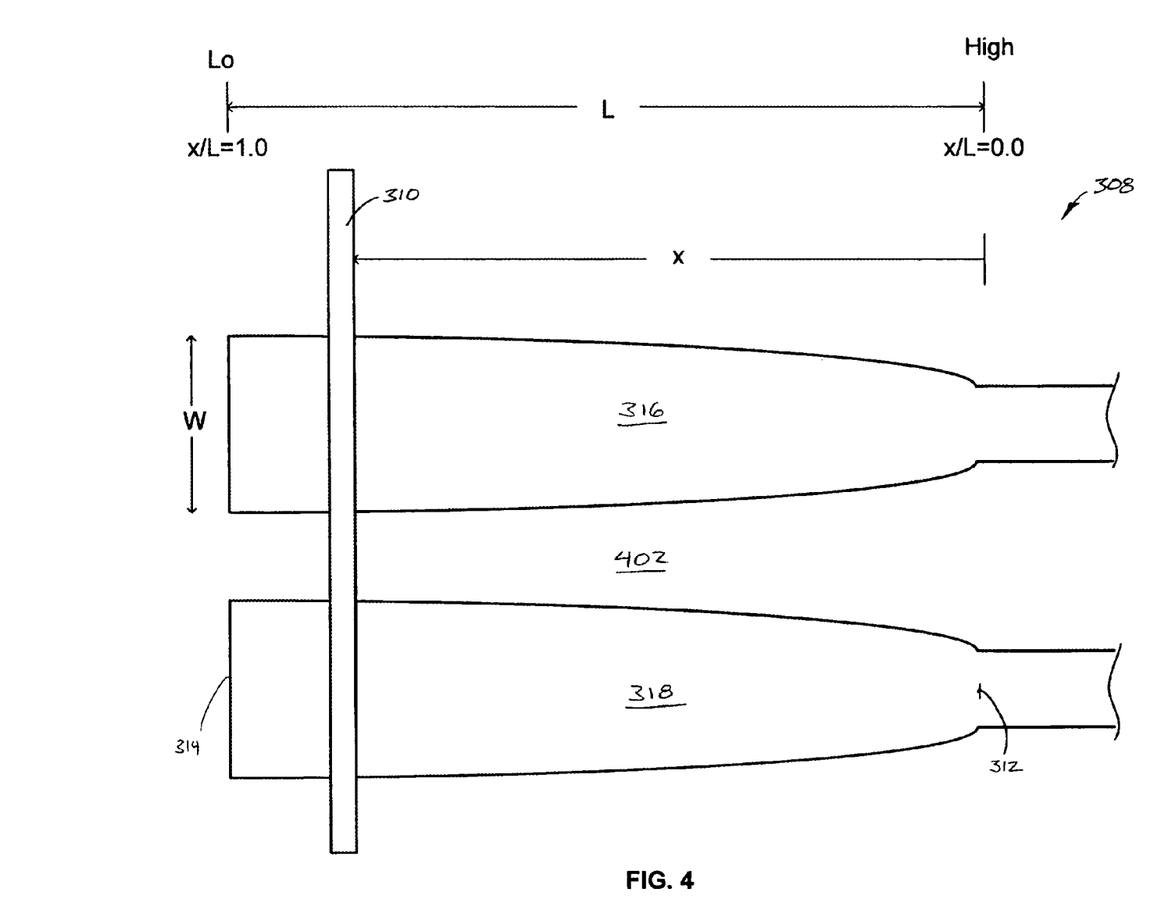
FIG. 4 depicts a fixed resistive element comprising a pair of thin-film resistors of varying widths.

Referring now to FIG. 4, a variable resistor in accordance with one embodiment of the present invention includes a pair of thin film resistor segments 316 and 318 of varying widths on a substrate 402. Moveable element 310 may be positioned at a distance x between ends 312 and 314 of the thin film resistors, which have a total length L. A dimensionless parameter d=x/L indicates the relative position of element 310 from "High" to "Low".

The combined resistance of thin film resistor segments 316 and 318 is equal to the integral of the relation given in equation (5) above over the length of the resistive elements contacted by moveable element 310, that is:

$$R(x) = \frac{2\rho}{t} \int_0^x \frac{1}{w(x)} dx \tag{6}$$

Figure 6:
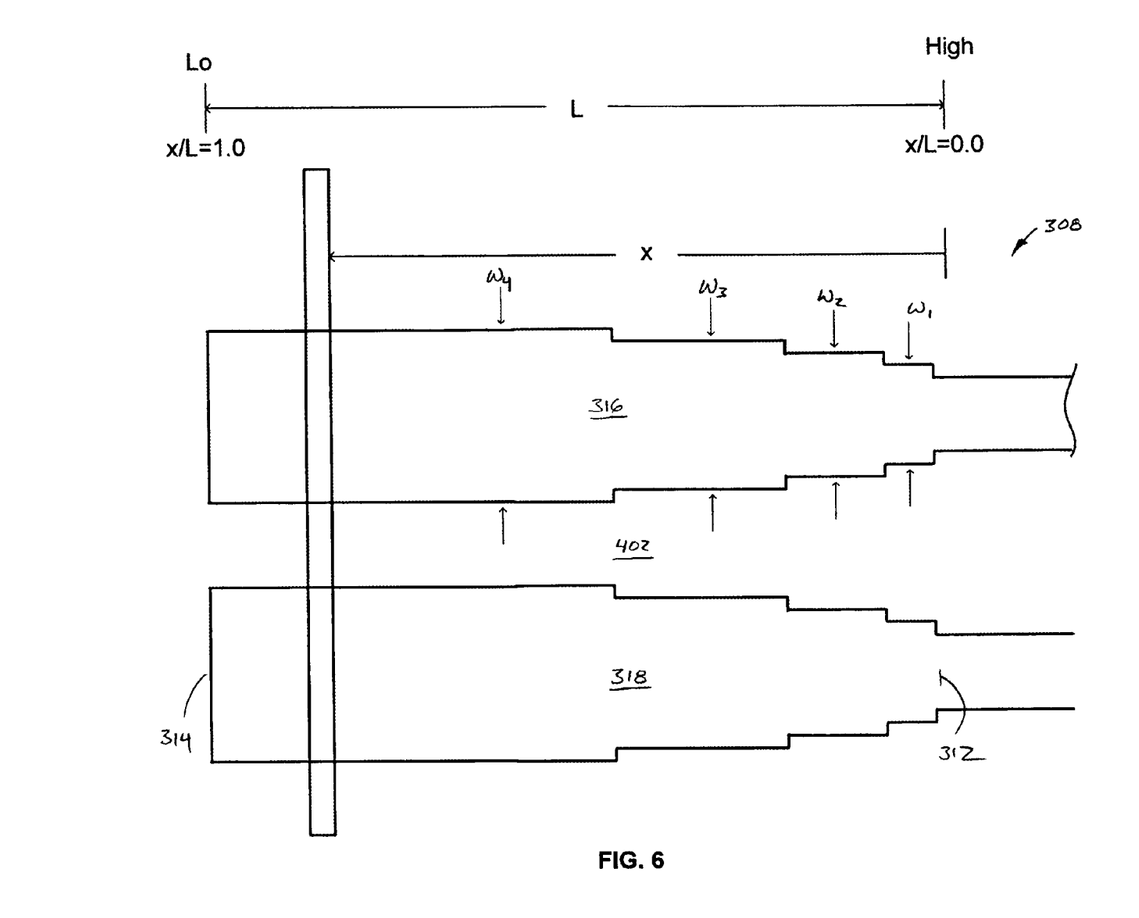
FIG. 6 depicts a fixed resistive element comprising a pair of thin-film resistors having discontinuous or "stepped" widths.

Utilizing equation (6), the width function w(x) may be selected to provide any suitable relationship between slider position (i.e., position of moveable element 310) and dissipated power. In this regard, w(x) may be a continuous function as illustrated in FIG. 4, or may be a discontinuous function. Referring to FIG. 6, for example, resistive elements 316 and 318 may be formed in a "stair-step" configuration characterized by a plurality of contiguous rectangular shapes in series from one end (312) to the other (314). In the illustrated embodiment, for example, thin-film resistors 316 and 318 each have four discrete widths at various points along their lengths.

In accordance with one embodiment of the present invention, the variable resistance is proportional to the square root of the slider position, e.g., $R_S = R_{max}\sqrt{d}$. A variety of other mathematical relationships may be desirable in a particular context, including, for example, a logarithmic function, a polynomial function, or a combination thereof. Alternatively, the width of the various thin-film resistors may be determined empirically and/or through the use of iterative techniques such as finite element analysis. Furthermore, the various thin-film resistors may be laser trimmed in-situ to further customize their characteristics.

Figure 9A:
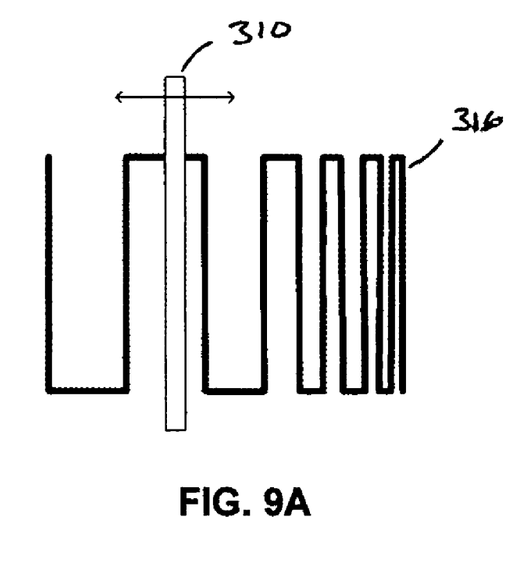
FIGS. 9A and 9B depict thin film resistive elements in according with alternate embodiment of the present invention.
Figure 9B:
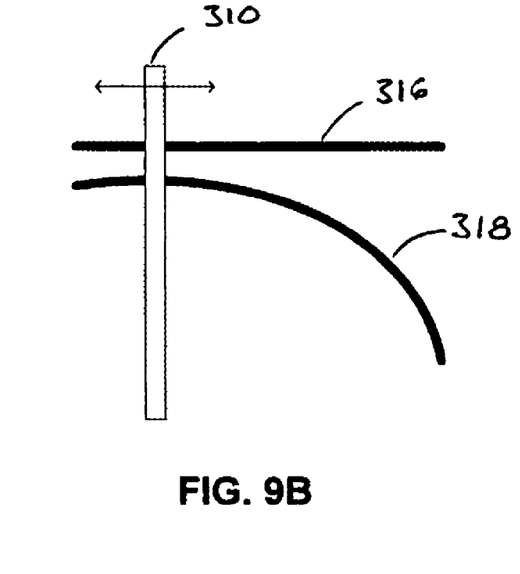

While the embodiments shown in FIGS. 4 and 6 depict thin-film resistors with substantially identical shapes, it will be appreciated that the present invention contemplates embodiments wherein the thin-film resistors differ in shape and type. For example, thin-film resistor 316 may have a series of discrete widths while at the same time thin-film resistor 318 has a continuously varying width. Furthermore, as shown in FIGS. 9A and 9B, the thin-film resistor may include any number of geometrical variations which achieve the desired variation in resistance. For example, referring to FIG. 9A, thin film resistor 316 may comprise a serpentine pattern of thin-film material in having a diminishing pitch. Alternatively, as shown in FIG. 9B, the shapes of one or more of the thin film resistors may be modified such that the geometric relationship between the two curves results in the desired relationship between the position of moveable element 310 and total resistance. In the illustrated embodiment, for example, thin film resistive element 318 diverges from element 318 in accordance with an exponential or polynomial function.

Figure 7:
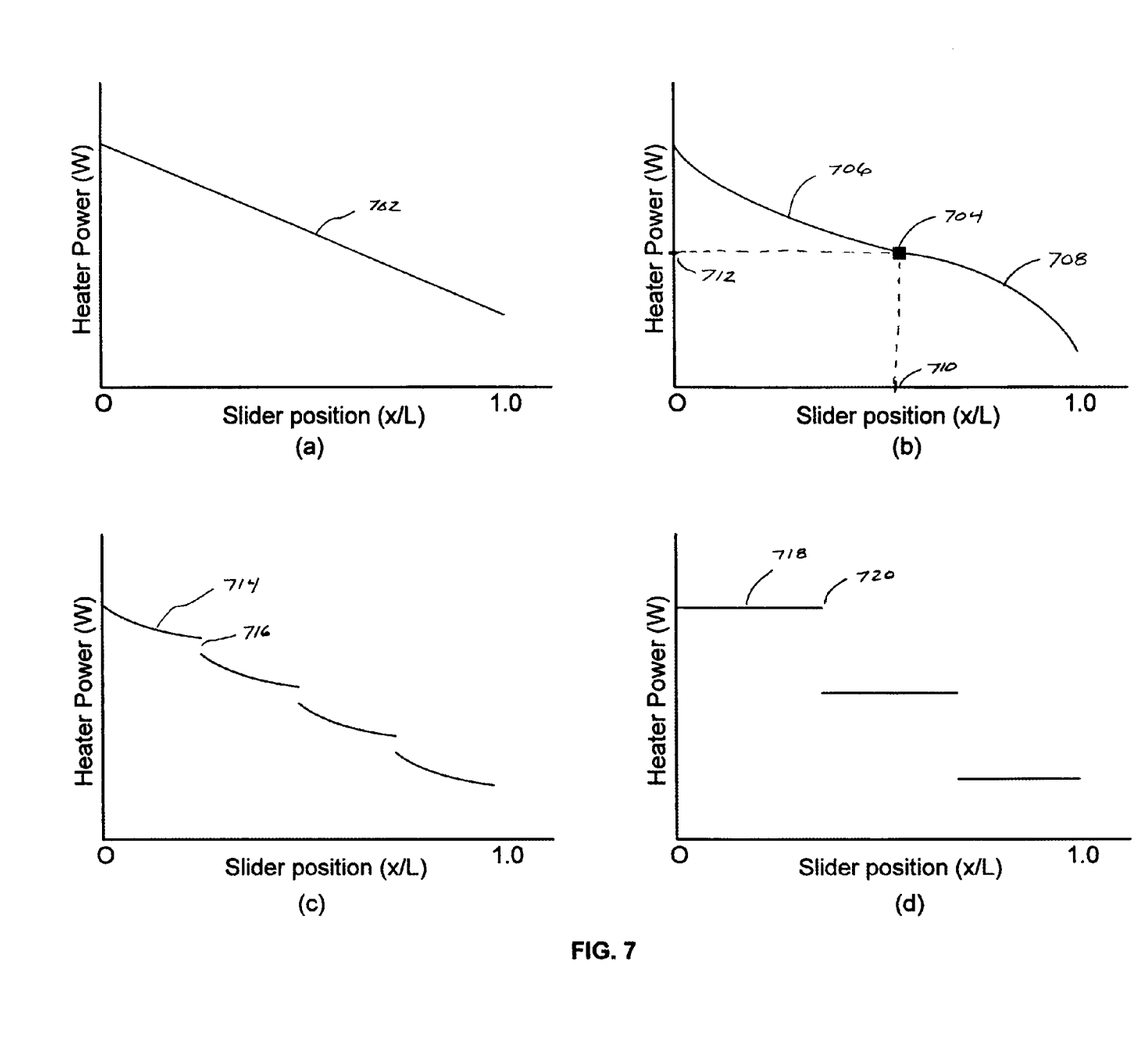
FIGS. 7A–7D are qualitative graphs of exemplary relationships between dissipated heater power and slider position.

The configuration of thin-film resistors 316 and 318 may be selected to produce a power/position curve which is at least partially linear in a number of respects. Referring now to the exemplary graphs shown in FIGS. 7A–7D, the fixed resistive element may be configured to produce any suitable relationship between dissipated power and slider position. For example, as shown in FIG. 7A, the power/position curve 702 may be substantially linear within its operation range. That is, while equation (3) above is itself non-linear, it is continuous, and therefore may be manipulated (through the choice of a suitable relation for $R_s$) to produce a curve which has a linear appearance within a desired range.

FIG. 7B shows an embodiment wherein the power/position curve is non-linear but includes a predetermined point 704 corresponding to a dissipated power 712 and slider position 710 substantially coinciding with the desired linear relation. That is, as illustrated in FIG. 7B, the half-way point for dissipated power (712) corresponds to the half-way point for slider position (710), even though curves 706 and 708 on either side of point 704 are non-linear. This embodiment is particularly desirable in systems which include "high", "low", and medium settings.

Alternatively, as shown in FIG. 7C, the curve may be discontinuous in that it includes a plurality of non-linear segments 714 separated by discontinuities 716. The embodiment shown in FIG. 6 may be configured to exhibit such a relation. Similarly, as shown in FIG. 7D, the curve may be discontinuous in that it includes a plurality of discrete constant power regions 718 separated by discontinuities 720.

While the curves shown in FIGS. 7A–7D are monotonically decreasing, the present invention contemplates that the dissipated power might actually rise briefly within one or more regions of the curve. That is, as long as the dissipated power curve is at least partially linear in the sense that the system exhibits substantially linear behavior within a particular range or for particular values, then the variable resistor may be configured such that the dissipated power has a periodic or other non-monotonic characteristic.

Figure 8:
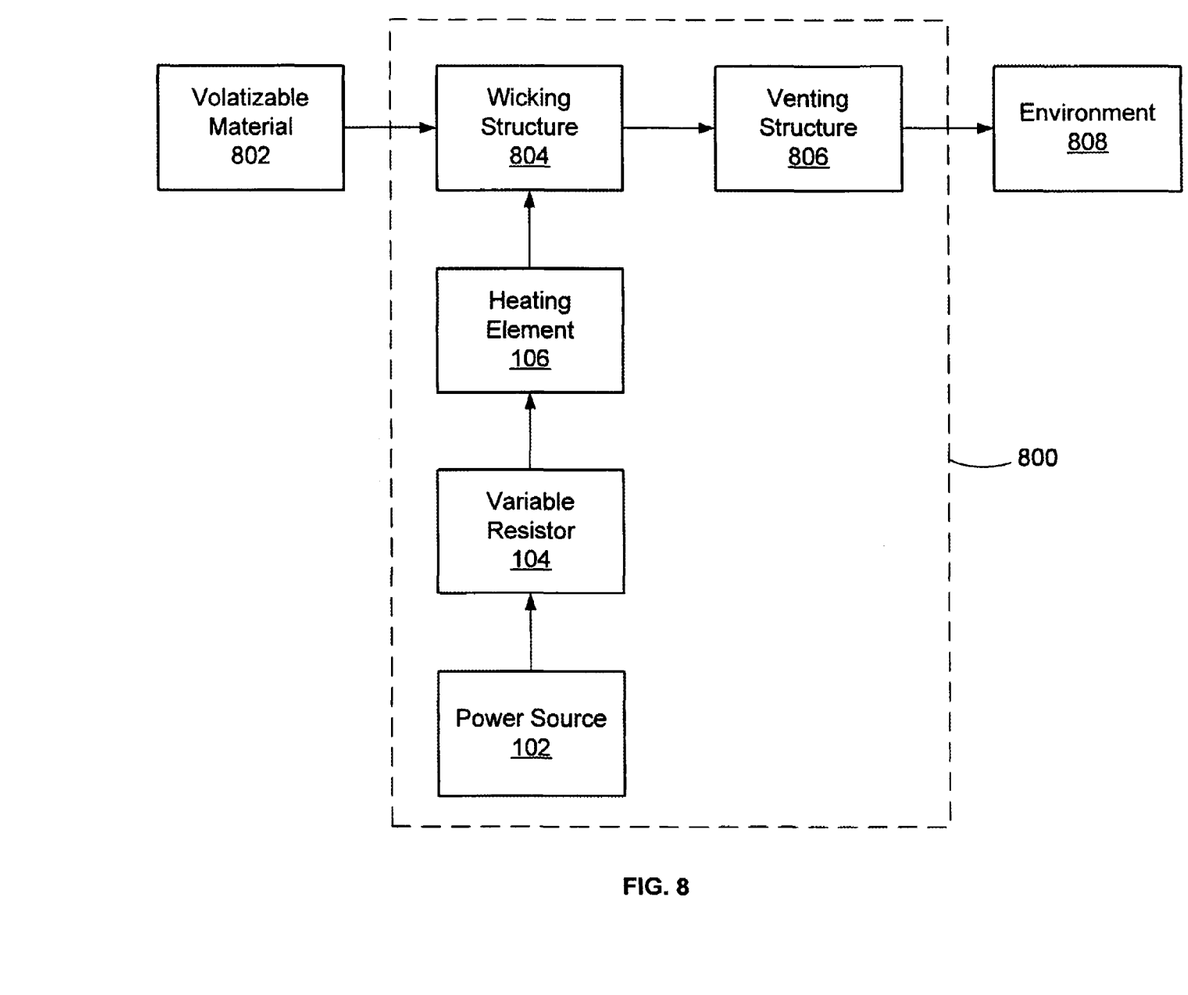
FIG. 8 is a schematic block diagram of a system employing a controllable heater in conjunction with a vapor delivery device in accordance with the present invention.

FIG. 8 presents a block-diagram of a system in accordance with one application of the present invention wherein a volatizable material such as an oil, wax, or the like is delivered to an environment 808 via an exemplary material delivery system 800. As shown, material delivery system 110 may suitably comprise a wicking structure 804 coupled volatizable material 802 and optional venting structure 806. Wicking structure 804 is thermally coupled to heating element 106 (e.g, any of the various resistive elements described above), the temperature of which is suitably controlled via variable resistor 104. Heating element 506 is electrically coupled to a power source 102, wherein power source 102 comprises any voltage/current source capable of providing the necessary current and voltage for heating element 106 as described above. Suitable power sources include, for example, standard household AC outlets, one or more batteries, solar power, etc.

In accordance with an exemplary embodiment, material delivery system 800 and volatizable material 802 form a self-contained unit that includes one or more plugs configured to attach to an electrical receptacle, for example, a duplex AC power outlet. The heating element 106 then receives power indirectly from the AC outlet—i.e., through appropriate fixed and/or variable resistors. One or more fuseable links may be included to the circuit to prevent potential damage resulting from over-current conditions.

Further in accordance with an exemplary embodiment, wicking structure 804 includes an eminator pad (or simply "pad") which may or may not comprise the same material used for other components of wicking structure 502, which is thermally coupled to a thin film resistive element capable of heating the eminator pad to a range of surface temperatures. The thermal coupling wicking structure 804 and heating element 106 may be in the nature of conduction, convection, radiation, or a combination thereof. In one embodiment, for example, heat transfer between wicking structure 804 and heating element 106 is accomplished primarily through conduction. That is, wicking structure 804 may directly contact heating element 106 (through, for example, an interference fit and/or a compressive load) or may be thermally coupled to heating element 106 through one or more intermediary layers of plastic or other material.

In summary, the present invention provides methods and apparatus for an improved variable resistor configured to at least partially compensate for non-linearities in an electrical circuit containing a heating element.

The present invention has been described above with reference to various exemplary embodiments. However, many changes, combinations and modifications may be made to the exemplary embodiments without departing from the scope of the present invention. For example, the various components may be implemented in alternate ways. These alternatives can be suitably selected depending upon the particular application or in consideration of any number of factors associated with the operation of the system. In addition, the techniques described herein may be extended or modified for use with other types of devices.

What is claimed is:

1. A vapor delivery system for dispensing a vaporized material having a controllable heating apparatus comprising:
    a heating element;
    a voltage source coupled to said heating element;
    a variable resistor coupled to said heating element and said voltage source, said variable resistor including a fixed resistive element and a moveable element, said moveable element having a position and adjustably contacting said fixed resistive element at a contact point associated with said position;
    said fixed resistive element having a length and comprising a first thin film resistor and a second thin film resistor substantially parallel to said first thin film resistor, said first and second thin film resistors having a width that varies non-linearly over said length
    said variable resistor having a resistance that is at least partially non-linearly related to said position;
    said heating element having a dissipated power that is at least partially linearly related to said position, said dissipated power at least partially linearly related to a temperature of said heating element.

2. The controllable heating apparatus of claim 1, wherein said heating element comprises a thin-film resistor.

3. The controllable heating apparatus of claim 2, wherein said heating element comprises a thin-film resistor having a serpentine pattern.

4. The controllable heating apparatus of claim 1, wherein said voltage source comprises an AC power source.

5. The controllable heating apparatus of claim 1, further including a vapor dispensing device thermally coupled to said heating element, said vapor dispensing device configured to release vapor into an environment at a rate that is a function of said dissipated power.

6. The controllable heating apparatus of claim 1, wherein said moveable element comprises a component selected from the group consisting of a slider switch, a dial, a knob, a screw, and a thumbwheel.

7. The controllable heating apparatus of claim 1, wherein said fixed resistive element comprises at least one thin film resistor.

8. The controllable heating apparatus of claim 7, wherein said at least one thin film resistor has a first end, a second end, and an attribute that varies non-linearly between said first end and second end, said attribute selected from the group consisting of width, thickness, material, and sheet resistance.

9. The controllable heating apparatus of claim 1, wherein said width varies continuously over said length in accordance with a geometric function selected from the group consisting of a square-root function, a logarithmic function, and a polynomial function.

10. The controllable heating apparatus of claim 1, wherein said width varies in accordance with a period of discrete steps.

11. The controllable heating apparatus of claim 1, wherein said moveable element has a high position, a low position, and at least one intermediate position between said high and low positions, and wherein said dissipated power at said high, low, and intermediate position define a substantially linear curve.

12. A variable resistor for controlling a heating element in a vapor delivery system for dispensing a vaporized material coupled in series with a voltage source V, the heating element being of the type characterized by a resistance RH and a dissipated power PH=IVH, wherein I is the current through the heating element and VH is the voltage across the heating element, said variable resistor comprising:
  a fixed resistive element having a length L;
  a moveable element having a position x adjustably contacting said fixed resistive element at a contact point associated with said position x;
  said fixed resistive element having a resistance RS(x);
  wherein the dissipated power PH is related to RS(x) by the equation:

$$P_H = C_1 \left( \frac{1}{R_S^2 + C_2 R_S + C_3} \right)$$

where $C_1 = V^2 R_H$, $C_2 = 2R_H$, and $C3 = R_H^2$;
  said dissipated power linearly related to a temperature of said heating element;
  and wherein RS(x) is a non-linear function and PH(x) is at least partially linear.

13. The variable resistor of claim 12, wherein $R_S(x) \propto \sqrt{x/L}$.

14. The variable resistor of claim 12, wherein said fixed resistive element comprises two substantially parallel thin film resistors having widths w which vary non-linearly as a function of x.

15. The variable resistor of claim 12, wherein $w(x) \propto \sqrt{x/L}$.

16. The variable resistor of claim 12, wherein said moveable element has a high position $X_{high}$, a low position $X_{low}$, and at least one intermediate position, wherein said dissipated power $P_H$ has a curve which substantially intersects a line defined by $(X_{high}, P_H(X_{high}))$ and $(X_{low}, P_H(X_{low}))$ at three points along said curve.

* * * * *